(12) United States Patent
Höfler et al.

(10) Patent No.: US 12,138,087 B2
(45) Date of Patent: Nov. 12, 2024

(54) CONTAINER SYSTEM AND METHOD FOR FORMING A KNOB IN A CONTAINER

(71) Applicant: Aesculap AG, Tuttlingen (DE)

(72) Inventors: Martina Höfler, Trossingen (DE); Gerold Zieris, Tuttlingen-Möhringen (DE); Matthias Schweizer, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 370 days.

(21) Appl. No.: 17/289,278

(22) PCT Filed: Oct. 28, 2019

(86) PCT No.: PCT/EP2019/079343
§ 371 (c)(1),
(2) Date: Apr. 28, 2021

(87) PCT Pub. No.: WO2020/089143
PCT Pub. Date: May 7, 2020

(65) Prior Publication Data
US 2021/0393363 A1    Dec. 23, 2021

(30) Foreign Application Priority Data
Oct. 29, 2018   (DE) ............ 10 2018 126 975.7

(51) Int. Cl.
*A61B 50/30*   (2016.01)
*A61B 90/90*   (2016.01)
(Continued)

(52) U.S. Cl.
CPC ............ *A61B 50/30* (2016.02); *A61B 90/90* (2016.02); *B21D 35/002* (2013.01); *A61B 2050/005* (2016.02)

(58) Field of Classification Search
CPC ............ A61B 90/90; A61B 2203/00; A61B 2050/005; A61B 50/30; B65D 5/4212
(Continued)

(56) References Cited

U.S. PATENT DOCUMENTS 5,299,700 A * 4/1994 Beniacar ............ B65D 23/0857
220/23.91
5,415,904 A   5/1995 Takubo et al.
(Continued)

FOREIGN PATENT DOCUMENTS

CN   105414363 A   3/2016
DE        293296 C   8/1912
(Continued)

OTHER PUBLICATIONS

International Search Report received in Application No. PCT/EP2019/079343 dated Dec. 16, 2019, with translation, 7 pages.
(Continued)

*Primary Examiner* — Steven A. Reynolds
(74) *Attorney, Agent, or Firm* — Christopher A. Rothe; CM Law

(57) ABSTRACT

A container system and a method for forming a knob in a container. The container system includes a container, in particular a medical or surgical sterile container preferably having a tub-like container vessel and/or a container cover; at least one separate coupling element; and at least one coupling system for releasably connecting the coupling element to the container. The coupling system includes a male coupling portion formed on the container and a female coupling portion formed on the coupling element. The coupling portions can be coupled to and uncoupled from one
(Continued)

Figure 1:
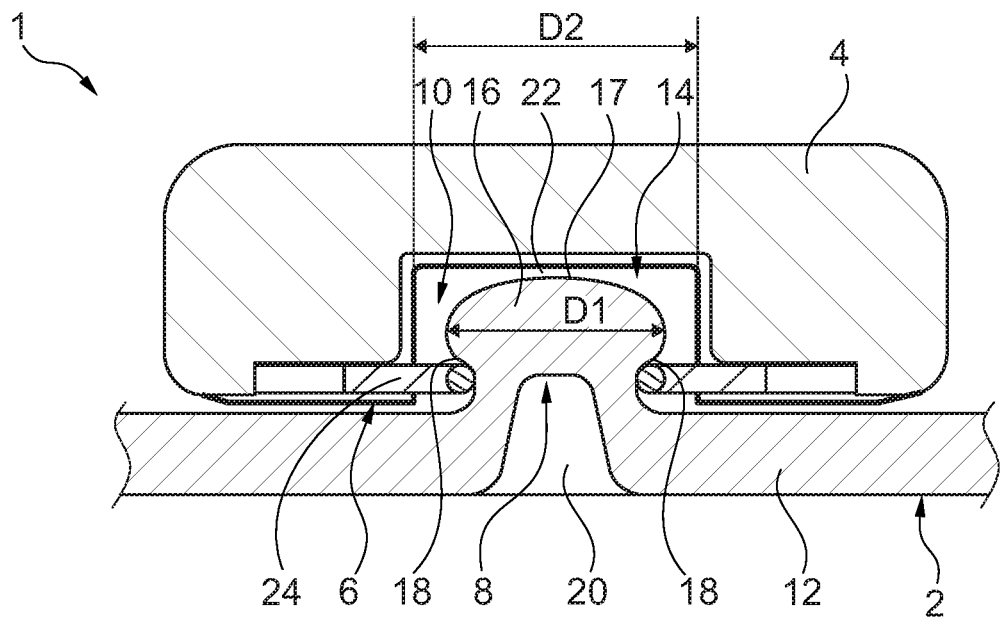

another. The male coupling portion is integrally formed in a wall of the container and is designed as a protruding knob having an undercut.

17 Claims, 4 Drawing Sheets

(51) Int. Cl.
  *B21D 35/00* (2006.01)
  *A61B 50/00* (2016.01)
(58) Field of Classification Search
  USPC .............................................. 206/459.1, 438
  See application file for complete search history.

(56) References Cited

U.S. PATENT DOCUMENTS

| | | | |
|---|---|---|---|
| 8,469,939 B2 | 6/2013 | Fangrow, Jr. | |
| 2006/0091030 A1* | 5/2006 | Tawanapoor | A47G 19/24 206/320 |
| 2017/0224434 A1* | 8/2017 | Schwartzbauer | A61B 50/33 |
| 2019/0358357 A1* | 11/2019 | Bohnenstengel | A61L 2/26 |

FOREIGN PATENT DOCUMENTS

| | | |
|---|---|---|
| DE | 69319171 | 11/1998 |
| DE | 102016011795 A1 | 4/2018 |
| EP | 1952964 B1 | 5/2012 |
| GB | 453055 A | 9/1936 |
| KR | 101195042 B1 | 10/2012 |
| WO | 2013155005 A1 | 10/2013 |
| WO | 2018104390 A1 | 6/2018 |

OTHER PUBLICATIONS

Search Report received in German Application No. 10 2018 126 975.7 dated Jul. 25, 2019, with translation, 15 pages.
Written Opinion received in Application No. PCT/EP2019/079343 dated Dec. 16, 2019, with translation, 14 pages.
Office Action received in Chinese Application No. 201980067600.0 dated Sep. 20, 2023, with translation, 13 pages.
Office Action received in Chinese Application No. 201980067600.0 dated Apr. 25, 2024, with translation, 12 pages.

* cited by examiner

CONTAINER SYSTEM AND METHOD FOR FORMING A KNOB IN A CONTAINER

CROSS-REFERENCE TO RELATED APPLICATION(S)

This application is the United States national phase entry of International Application No. PCT/EP2019/079343, filed Oct. 28, 2019, and claims the benefit of priority of German Application No. 10 2018 126 975.7, filed Oct. 29, 2018. The contents of International Application No. PCT/EP2019/079343 and German Application No. 10 2018 126 975.7 are incorporated by reference herein in their entireties.

FIELD

The present invention relates to a container system comprising a container, in particular a medical or surgical sterile container preferably having a tub-like container vessel and/or a container cover; at least one separate coupling element and at least one separate coupling system for releasably connecting the coupling element to the container, wherein the coupling system comprises a male coupling portion formed on the container and a female coupling portion formed on the coupling element, which coupling portions can be coupled to and uncoupled from one another. In addition, the invention relates to a (forming) method for forming a knob in or on a container, particularly a medical or surgical sterile container preferably including a tub-like container vessel and/or container cover.

BACKGROUND

In the prior art, various forms of connection to a container or a container system with a coupling system are shown. A releasable connection system/coupling system according to the known prior art is, for example, screws. These are screwed into the body of a container, such as a sterile container, and releasably fix another component or coupling element to the sterile container. In particular, closure systems or identification labels can be attached in this way. Clamps can also be used, for example, which clamp the element to be connected in a force-fit manner. However, the clamps must also be fastened to the container, which is usually done by riveting. Furthermore, securing systems or closure systems by means of positive locking or snapping hooks, which are fastened to the container, are known from the prior art.

However, one problem of the prior art is that the known connection or coupling systems require an opening for a fixed connection and thus cause a penetration point in a component. These penetration points are potentially permeable to germs or are not leak-proof to germs and also are difficult to clean or disinfect. In addition, due to capillary action, water as well as blood and other bodily secretions can be drawn into the gap. The gap, as well as other geometries that are difficult to clean, therefore harbor the risk of recontamination at these points, which is why the container system does not meet the requirements for sterility. This also complicates the production process and increases production costs.

In addition, some coupling variants require a large number of components, which must also be assembled after production. These cause an increased production effort and can be lost or forgotten, especially since they often are not firmly connected to the other components. This makes handling much more difficult, as it is necessary to check the correct number of components, e.g. by using a list. If, for example, clip systems with snap-in noses are used on screen baskets for releasable fastening of signs which can be hooked into the screen structures of the screen basket, corresponding geometries with openings and undercuts are required.

SUMMARY

It is therefore the object of the invention to avoid or reduce the disadvantages of the prior art and, in particular, to provide a container system and a method for producing such a container system with a coupling system by means of which further coupling elements can be releasably attached/fastened to a container, wherein such a connection or such a coupling system is to be easy to clean and is to form a germ-tight connection.

Moreover, the number of required components is to be minimized for good handling and inexpensive production.

According to the invention, the object of the invention in a generic container system is solved in that the male coupling portion is integrally/materially formed/shaped in a wall of the container and is designed in the form of a protruding knob/protruding mushroom with an undercut. In this case, the knob has a mushroom-shaped structure similar to a bollard or a champagne cork. A decisive feature of the male coupling portion is that it is formed integrally in the wall of the container itself, for example by forming (deep-drawing) the container wall, so that the wall of the container (container wall) continues to be maintained as a sterile boundary through which no bacteria, virus or fluid can penetrate and no further component has to be produced, as well as that the protruding knob forms an undercut in order to positively attach further coupling elements, such as an identification plate, to the knob via the formed undercut. In particular, the knob has a rounded head and is therefore particularly suited for being cleaned or sterilized. The coupled state is the state in which the male coupling portion and the female coupling portion are in operative engagement with one another and the coupling element is thus coupled to the container, and the uncoupled state is to be comprehended as a state in which the female and male coupling portions are no longer in operative engagement with one another and the container and the coupling element are not fixed to one another but can be freely arranged. The user is provided with a container system that can be used individually, has a reduced risk of injury due to rounded edges in particular, and implements simple coupling/assembly and decoupling/disassembly of coupling elements. The formation of the knob eliminates the need for further separate components.

In a preferred embodiment, the coupling system may be in the form of a push-button system in which the female coupling portion (push-button) has a circular recess into which the knob (its knob head) protrudes/is pressed in a coupled state, the undercut of the knob being encompassed/enclosed by the female coupling portion resiliently/in a prestressed manner. Due to the fact that the coupling system is formed as a push-button system and the female coupling portion encompasses/encloses the knob in a prestressed manner, the limit of a tensile force is defined which is required to disengage the female coupling portion from the male coupling portion. Thus, a minimum force is required for disengagement from the knob, which can be adjusted according to the pretension, ensuring that the female coupling portion does not disengage unintentionally.

Preferably, the female coupling portion can have an undercut, in particular a circumferential undercut, which encompasses the undercut of the knob and releasably couples the knob by means of material elasticity/inherent elasticity, or the female coupling portion can have a separate spring which encompasses/encloses the undercut of the knob in order to releasably couple the knob. Different variants are conceivable for implementing the preload. On the one hand, an inwardly pointing undercut can also be formed on the female coupling portion, for example, by a circumferential bar, whereby this undercut can widen under a force effect due to material elasticity in order to increase the inner diameter of the undercut. Thus, when the user pulls the female coupling portion from the male coupling portion in the coupled state, the knob presses the undercut apart due to the tensile force and its funnel-shaped geometry on its rear/bottom side, so that the undercut enlarges and can be pulled off over the knob. On the other hand, the female coupling portion may have a spring, whereby this spring forms an undercut and encompasses the head of the knob in a resilient or prestressed manner. If a tensile force is now applied to the female coupling portion in the coupled state, the geometry of the knob, as described above, causes the spring to be pushed apart, a distance between the arms of the spring increases and the female portion can ultimately be pulled off the male section. In particular, the spring may have two diametrically opposed and substantially parallel arms. Alternatively, the spring may be in the form of a Seeger ring that is set into a circumferential groove in the female coupling portion.

According to a further alternative aspect, the female coupling portion may comprise a recess in the form of a keyhole with a round insertion portion and a detent portion with parallel undercuts in the form of guide bars, which recess is configured such that the knob can be received in and removed from the insertion portion and is positively coupled via the guide bars after the knob was shifted into the detent portion.

In another preferred alternative embodiment, the female coupling portion may be formed in the form of two diametrically opposed snap-in noses which, in a coupled state, encompass the knob and thus couple the male coupling portion. The snap-in noses may have a defined material elasticity so as to be resilient in combination with their geometry, particularly through a long extended arm. Thus, the snap-in noses may be "clipped onto" the knob by way of compressive force and may be pulled off again by applying a tensile force. Preferably, the female coupling portion also may comprise a plurality of snap-in noses, in particular three, four or five snap-in noses, which encompass the knob in a coupled state. In particular, the snap-in noses are equally spread over the circumference.

Preferably the container is a sterile container and the coupling element is an identification label or an identification bezel or a perforation field cover or a sensor or an identification element or a holding element. The sensor may be, for example, a temperature sensor which records a temperature history. The identification element may be an identification label/tag of a tracking system/traceability system, such as an RFID chip of an RFID system for identifying the container. The holding element may be, for example, a holding clamp.

Alternatively or additionally, the container may be a screen basket/sieve basket and the coupling element may be an identification label or identification bezel. In particular, the sterile container and the screen basket have an identical geometry of the knob, so that the coupling elements such as the identification label, can be coupled to both the sterile container and the screen basket. Thus, the user is provided with a modular container system similar to a construction kit, which makes it possible to use the coupling elements with different containers.

According to a further aspect of the invention the container system may comprise a second container as a coupling element, so that the first container can be "hooked into" the second container and can be coupled to it. Thus, if a knob protruding outwardly from the container is formed, for example, on one container wall and the complementary female locking portion is formed on an opposite outer side of the container, for example, in the form of an indentation formed inwardly of the container, two or even more containers can be hooked into one another.

Preferably, the container may include metal or a metal material, especially aluminium, or a metal alloy. Metals can be sterilized particularly well, are enduring and withstand stresses occurring in practice, such as temperature fluctuations, particularly well. Moreover, they can be processed well and are inexpensive. Depending on the application, an optimum composition of the metals or metal materials can be determined in metal alloys in order to obtain the best possible material for the container, particularly in terms of strength and chemical resistance. As material, aluminium is particularly advantageous since it is light, corrosion-resistant and moreover can be very easily sterilized. Also hardened and tempered steel with corresponding alloy contents or stainless steel are alternative metal materials for the container. In particular chrome and/or manganese and/or nickel and/or molybdenum and/or titanium and/or niobium and/or vanadium and/or cobalt may be used as alloy metals for a metal alloy.

According to a further aspect of the invention, the metal material or the metal alloy may make up at least 80 percent by weight (% by weight), preferably 90 percent by weight, of the container, and in particular the entire container may be made from the metal material or the metal alloy. In particular the medical or surgical sterile container may be made from the metal material or the metal alloy.

The container is preferably made by deep-drawing. The structural properties of the container are particularly favourable after deep-drawing. The containers can also be manufactured cost-effectively and efficiently. In particular the container tub is manufactured by deep-drawing.

With regard to the generic (forming) method the object of the invention is solved by the following steps according to the invention: Arranging two complementary press dies on opposite sides of a wall of the container, a male press die of the two press dies having a protrusion and a female press die having a complementary die recess; pressing the complementary press dies against each other and thereby squeezing/deep-drawing a cup projecting toward the outer side of the container; and compressing the cup so that a knob is formed/shaped with a head and a circumferential undercut. Due to the shape of the complementary press dies, which are arranged coaxially to each other, a cup/press cup with a cylindrical or conical circumferential wall and an end wall/end face, preferably parallel or curved, in particular spherically curved, to the container wall, is produced in the second step. The circumferential wall and the end wall/end face do not yet have an undercut. The undercut is only produced in the third step, in which the cup is compressed and in which the end wall and the adjacent area of the circumferential wall widen and form the undercut. Thus, by using the method of the invention, a knob can be formed in the container wall itself, thus maintaining a sterile boundary and also minimizing a number of components.

In a preferred alternative, the step of "compressing the cup" can be performed by a tool with a planar or spherical and preferably rotationally symmetrical die/stamp shape that flattens the cup to form the undercut by plastic deformation. The die shape can preferably have a polygonal contour or, viewed in cross-section, a polygonal circumference. In particular, the die shape has a hexagonal or octagonal contour.

According to an alternative variant, the step "compressing the cup" may comprise the following steps: Alternating the female press die with the male press die; and pressing the complementary press dies against each other. By changing the two pressing dies against each other, the cup can be compressed by means of the protrusion of the male pressing die. The number of different tools required can be minimized.

According to another alternative variant, the step of "compressing the cup" may comprise the steps of: Pressing the cup through a molding tool having a defined circumferential knob die contour into which the cup plastically presses and molds; and splitting the molding die and demolding the knob. In this alternative, the molding tool has an undercut shape. Due to the applied pressure, the cup is nevertheless pressed into the undercut mold, similar to injection molding, and conforms to the shape of the molding tool. After the pressing process, the at least two-part molding tool is split and the molding tool can be removed from the male coupling portion. This aspect of the invention makes special and individual shaping of the head of the knob possible.

According to one aspect of the invention, the steps of pressing the complementary press dies against each other and compressing the cup can be performed in a press-embossing step (substantially simultaneously) in which the two press dies are pressed against each other, the female press die being a molding tool having a defined circumferential knob die contour as an embossing mold into which the cup plastically presses and molds; and splitting the mold and demolding the knob. In this variant, the molding tool as female die has an undercut shape and by a single (translatory) press-embossing movement as a press-embossing step, namely pressing the two dies against each other, the cup is first deep-drawn over the protrusion of the male press die and shaped, and when further pressure is applied, plastic shaping takes place, as a result of the pressure, in the formed volume between the two press dies, in which the cup plastically presses, molds, and an undercut is formed.

BRIEF DESCRIPTION OF THE DRAWING FIGURES

Figure 2:
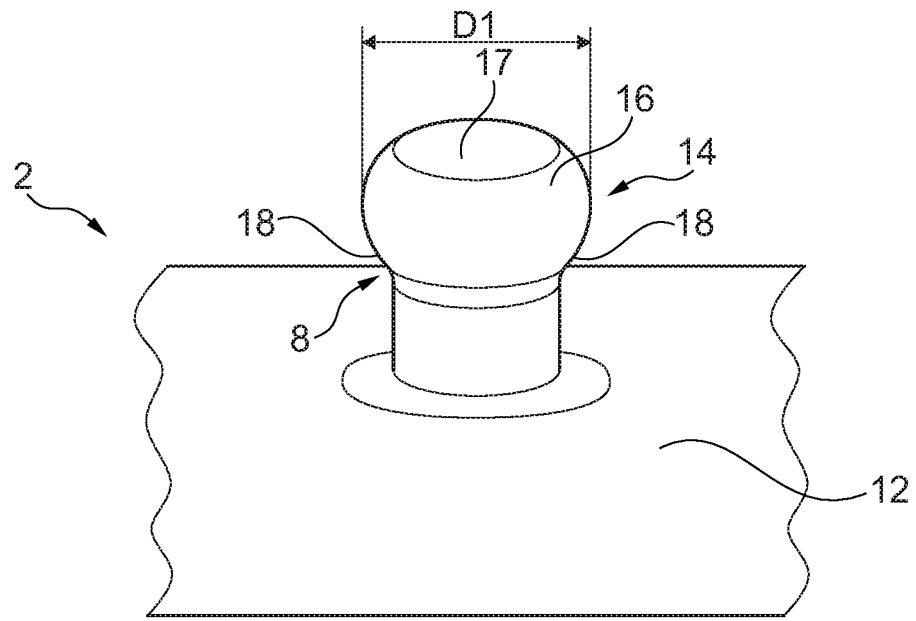
Figure 3:
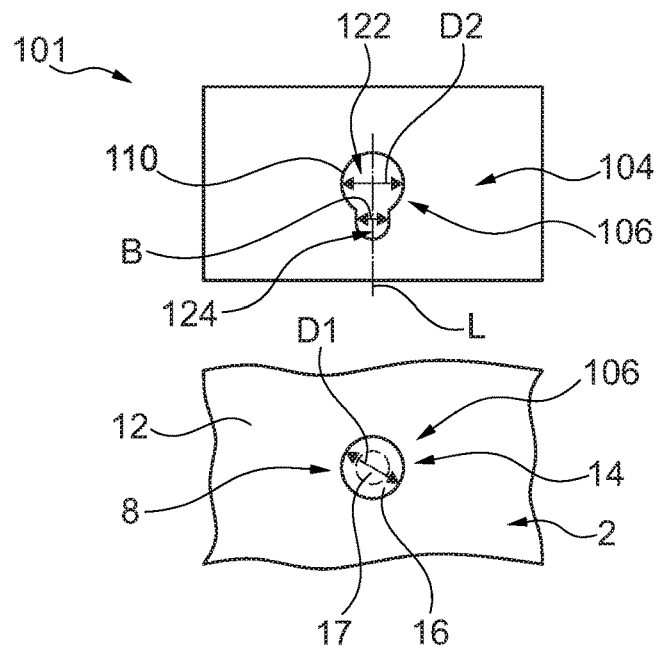
Figure 4:
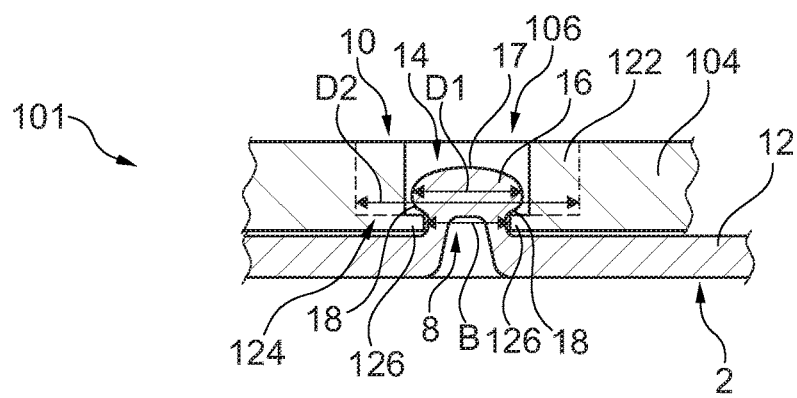
Figure 5:
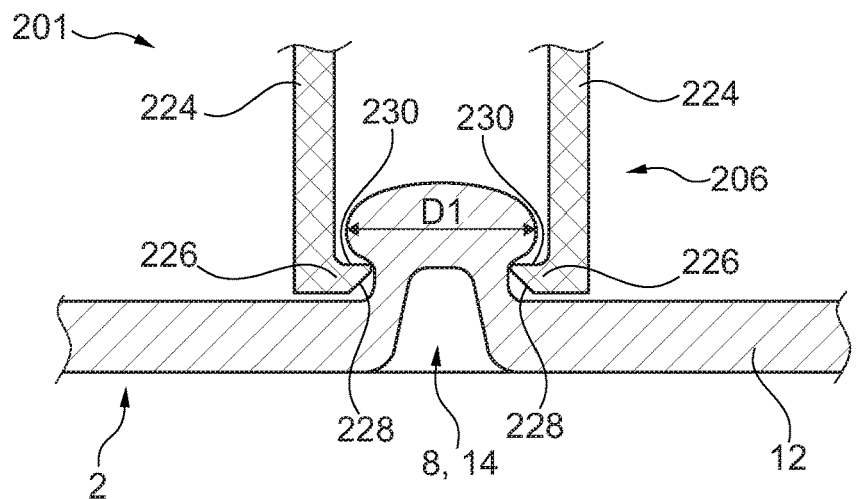
Figure 6:
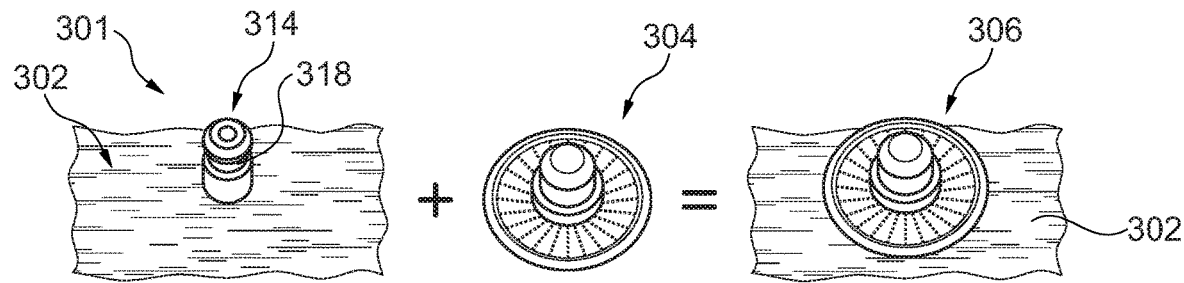
Figure 7:
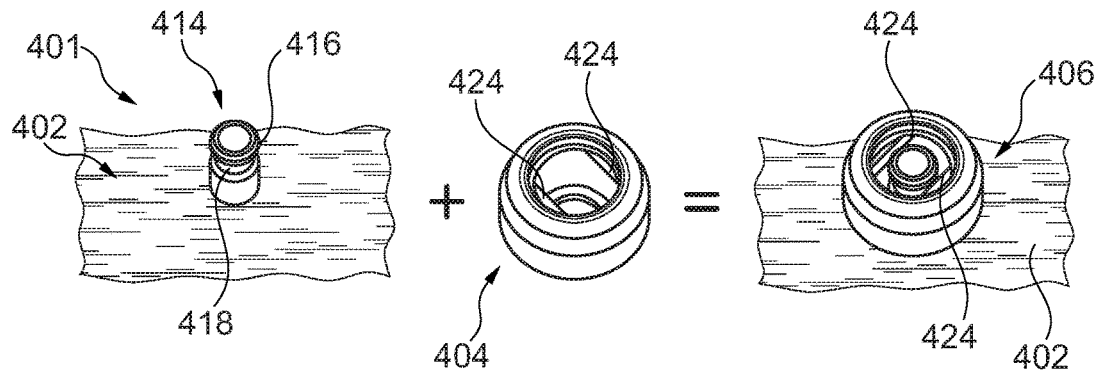

In the following, the invention is explained in more detail on the basis of preferred embodiments with the aid of accompanying figures, in which:

FIG. 1 shows a schematic cross-sectional view of the container system according to the invention with a coupling system of a first preferred embodiment, FIG. 2 is a perspective view of the knob of FIG. 1, FIG. 3 shows a schematic view of the container system according to the invention with a coupling system of a further, second preferred embodiment, FIG. 4 shows a cross-sectional view of the coupling system from FIG. 3, FIG. 5 shows a cross-sectional view of the container system according to the invention with a coupling system of a further, third preferred embodiment, FIG. 6 is a perspective view of the container system with a coupling system of a further, fourth preferred embodiment, FIG. 7 is a perspective view of the container system with a coupling system of a further, fifth preferred embodiment, and FIGS. 8 to 11 show cross-sectional views of the steps of the forming method according to the invention of a first preferred embodiment.

The figures are of a schematic nature and merely serve to comprehend the invention. Identical elements are provided with the same reference signs. The features of the various embodiments can be exchanged among each other.

DETAILED DESCRIPTION

In the following, embodiments of the present invention are described with the aid of the corresponding figures.

FIG. 1, in a cross-sectional view, shows a container system 1 according to the invention of a first preferred embodiment. The container system has two separate components/elements, i.e. on the one hand, a container 2 in the form of a tub-shaped sterile container or a tub-shaped screen basket or a container cover and, on the other hand, a coupling element 4 to be coupled thereto. In the embodiment, the coupling element 4 is an identification label indicating the contents of the container 2. In addition, further coupling elements 4 exist in the form of identification bezels and perforation covers for the container 2.

For coupling the coupling element 4, the container 2 has a coupling system 6 including a male coupling section 8 and a female coupling section 10. The male coupling section 8 is formed on the container 2, whereas the female coupling section 10 is formed on the coupling element 4. The male coupling section 8 is integrally/materially formed in a container wall 12 of the container 2, and has a protruding round knob 14 or a round mushroom 14. A head 16 of the knob 14 forms a circumferential undercut 18. The outer contour of the knob 14 has the shape of a bollard or champagne cork.

At the location of the knob 14 formed in the container wall 12, a concave, capsule-shaped and rotationally symmetrical recess 20 is formed within the knob 14. The opposite head 16 is shown in detail in FIG. 2 in a perspective view of the male coupling portion 8. The knob 14 is designed rotationally symmetrical with a circular contour and has a spherical head 16. The head 16 is flattened on its upper side 17. The circular head 16 with a diameter D1, which forms the circumferential undercut 18, engages in a circular recess 22 in the female coupling portion 10 with a diameter D2. In this case, the diameter D1 of the knob 14 is smaller than the diameter D2 of the recess 22 so that the knob 14 can be inserted therein. A spring element 24 in the form of a Seeger ring with round edges is enclosed in the coupling element 4 and in the coupled state encompasses/surrounds the head 16 of the knob 14 and thus the undercut 18. The spring has a diameter smaller than the diameter D1 of the head 16. By rounding off the edges of the undercut 18 or an even transition of the head 16 in combination with the rounded spring element, a click closure/clip closure in the form of a push-button system can be realized. Thus, a user can "clip on" the coupling element 4 to the container 2 by way of a compressive force (the spring 24 is expanded to a diameter larger than D1 against its pretension) and releasably connect it, as well as manually release it from the knob 14 by means of a tensile force (the spring 24 again is expanded to a diameter larger than D1 against its pretension). In this case, the knob 14 is integrally/materially shaped in the container 2, so that no sterile barrier is broken through and the container wall 12 provides a natural impermeable boundary.

FIG. 3 shows a schematic top view of container system 101 according to the invention of a further, preferred second embodiment with container 2 and with an alternative coupling element 104. In this embodiment the container system 1 has a coupling system 106 including the same male coupling portion 8, but a female coupling portion 110 configured differently with regard to the first embodiment. The female coupling portion 110, in top view, has a keyhole shape with a circular insert section 122 as well as a detent section 124 directly adjacent thereto. As already also in the first embodiment, the insert section 122 has a diameter D2 that is larger than the diameter D1 of the head 16 of the knob 14. However, the detent section, into which the insertion section 122 merges, has guide bars 126 that have a width B smaller than the diameter D1 of the head 16. As a result, the head 16 is gripped or held in the guide rails on both sides so as to be axially displaceable in the extension of a longitudinal axis L of the detent section 124, but axially fixed in a direction transverse thereto.

FIG. 5 shows a further alternative embodiment of a container system 201 according to the invention including a coupling system 206. The container 2 that includes the male coupling portion 8 is again held equally to the first two embodiments, whereas the coupling element 204 is configured differently. Specifically, the coupling element 204 has an alternative female locking portion 210. The female locking portion 210 is formed as two diametrically opposed locking hooks 224. In this regard, the two locking hooks 224 have snap-in noses 226 pointing towards each other, which have a ramp 228 on one side and a flat undercut 230 on an opposite side, so that they can be easily applied to the knob 14 in one direction with elastic deformation of the locking hook 224 by means of the ramp 228 and then hold the knob 14 positively in the axial direction via the undercut 230, and can be removed again from the knob 14 in an opposite direction with increased force (no helping ramp 228) and renewed elastic deformation. Alternatively, it is also conceivable that the two diametrically opposed locking hooks 224 can be manually shifted relative to one another, so that by such shifting the diameter is increased, allowing the coupling element 204 to be pulled off the knob 14 without elastic deformation.

FIGS. 6 and 7 each show a further container system 301 and 401 of a preferred fourth and fifth embodiment. In FIG. 6, the coupling element 304 has the shape of a hat and, similar to the first embodiment from FIGS. 1 and 2, is attached to knob 314.

FIG. 7, on the other hand, shows a coupling element 404 in the form of a bushing. Two parallel springs 424 run transversely to a longitudinal axis of the bushing within the bushing as female coupling portion 410. The springs 424 have a distance to each other that is smaller than the inner diameter of the bushing of the female coupling portion 410. The springs 424 hold the undercut 418 of the knob 414 or encompass/surround the head 416 of the knob 414 in a resiliently pretensioned manner. Thus, in the uncoupled state, the female coupling portion 410 can clip onto and couple to the male coupling portion 408 by way of a compressive force and, in the coupled state, can decouple again by applying a tensile force.

FIGS. 8 to 11 show steps of a (forming) method according to the invention of a preferred embodiment in order to manufacture the container system according to the invention including a knob 14 formed in one piece in the container 2, as depicted in FIG. 1.

Figure 8:
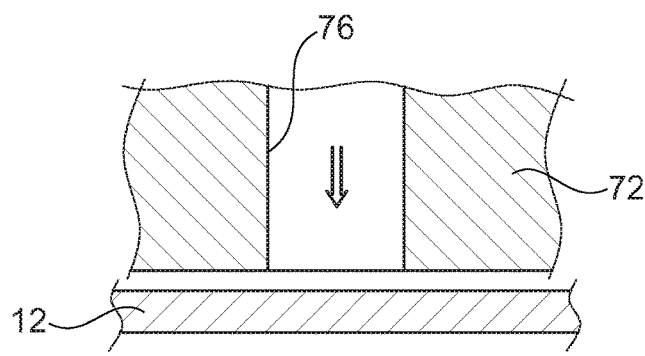
Figure 8:
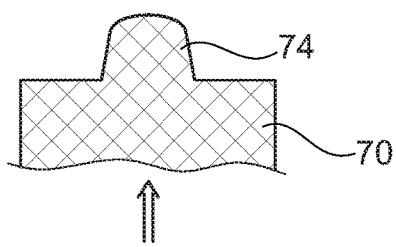

In FIG. 8, in a first step, the container wall 12 of the container 2, which in particular has aluminium as a material and is still flat/level or slightly curved at this point, is positioned and two complementary press dies 70 and 72 are arranged coaxially to each other on opposite sides of the container wall 12 at a predetermined point of the container wall 12 at which the knob 14 is to be formed eventually. In this case, the male press die 70 of the two press dies has a full-cylindrical protrusion 74 with rounded edges, and the female press die 72 has a die recess 76 complementary to the protrusion 74 in the form of a hollow cylinder with a circular through opening. The diameter of the protrusion 74 is less than the diameter of the through opening of the die recess 76, leaving a circumferentially wide gap between the protrusion 74 and the die recess 76 approximately equal to the thickness of the container wall 12 at the predetermined location of the knob 14. Alternatively, the gap may also have a thickness which is less than the thickness of the container wall. In particular, the thickness of the gap may be between 5% and 90% of the thickness of the container wall, more preferably between 10% and 70%, and most preferably between 20% and 40%.

Figure 9:
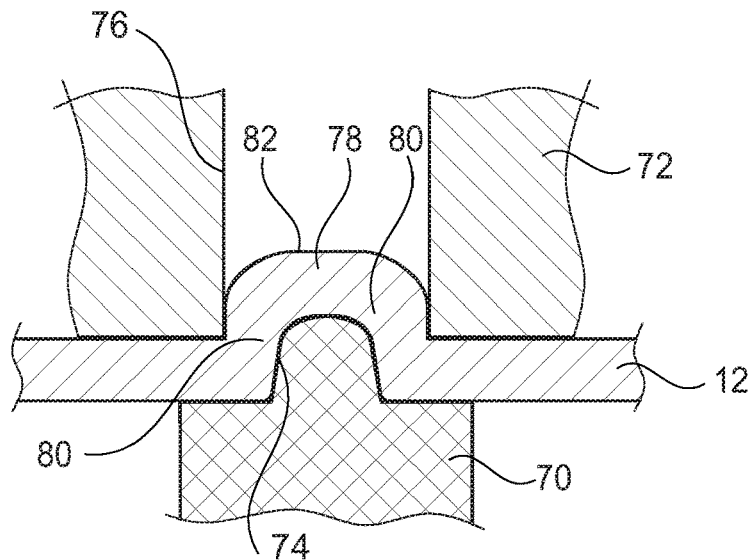

In a second step, the coaxially arranged complementary pressing dies 70, 72 are then moved against each other so that they first press on the container wall 12, or the tip of the protrusion 74 and the end portion of the hollow cylinder press on the container wall 12 and, after increasing the pressing force, the container wall 12 is pressed so that the area of the container wall 12 to be reshaped is plastically deformed and forms a cup 78. Squeezing or deep drawing of the cup 78 is effected, so to speak. This condition is shown in FIG. 9. The material or sheet metal of the container wall 12 thus adapts plastically to the die shape of the two complementary press dies 70, 72. The cup has a conical or cylindrical circumferential wall 80 and an end wall 82. After this second step, however, the cup 78 does not yet have an undercut.

Figure 10:
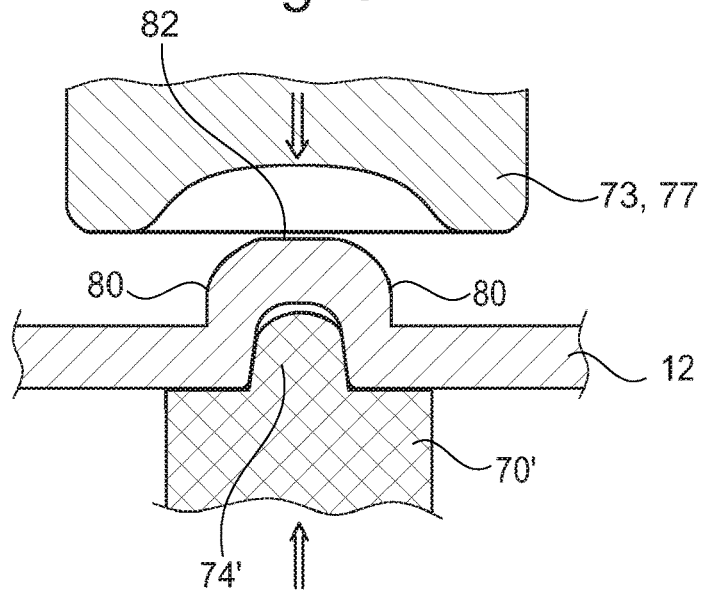
Figure 11:
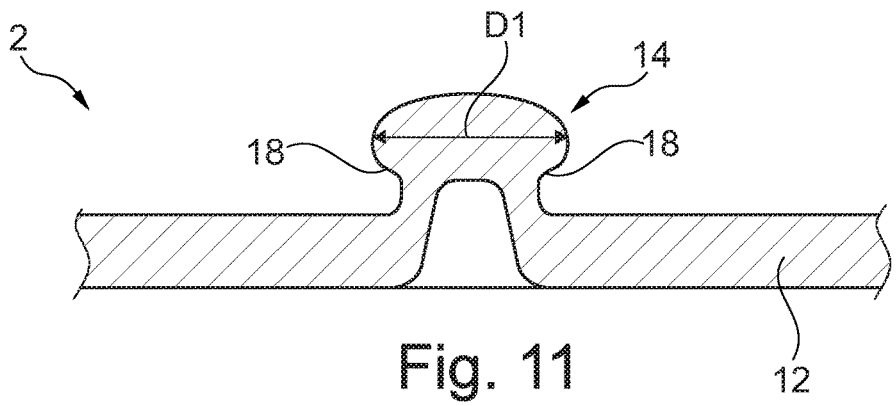

In a third step, the male press die 70 is exchanged for another, different male press die 70', which has a shorter protrusion 74'. Also, the female press die 72 is exchanged for a tool 73 with a spherical die/punch 77. This state is shown in FIG. 10. Following this, the male press die 72' is again moved against the tool 73 arranged coaxially to it and pressed against it with a pressing force. As a result of the geometries of the press dies or the tool, the cup 78 is plastically compressed or the cup 78 is plastically flattened and a knob 14 with a head 16 and a circumferential undercut 18 is formed, as shown in FIG. 11. The male press die 70 does not necessarily have to be replaced. In an embodiment not shown, the male press die 70 can also be maintained and only the female press die 72 can be replaced.

In this embodiment, the female press die 72 is tubular as a hollow cylinder with a through bore. In an alternative embodiment, instead of having an internal volume which is open in the upward direction in the longitudinal direction of the female press die 72, as depicted in FIG. 8, into which the container wall to be pressed fits and thus does not form a stop in the axial direction of the press die, the female press die may also have a punch shape which is closed in the upward direction, similar to the tool 73, as a stop in the axial direction, in in order to achieve, as it were, preforming of the head of the knob.

In one embodiment, the male coupling portion, of course, also may be formed with a polygonal circumferential wall having a polygonal contour, such as a pentagonal contour, a hexagonal contour, a heptagonal contour, or an octagonal contour, instead of a cylindrical or conical circumferential wall having a circular contour or circular cross-section. Alternatively, the circumferential wall also may have an elliptical contour. In particular, the two press dies also have a polygonal contour, such as a pentagonal contour, a hexagonal contour, a heptagonal contour or an octagonal contour, in the case of the female press die on the inner circumference and in the case of the male press die on the outer circumference of the protrusion.

In a further embodiment the rotationally symmetrically configured knob 14, instead of a circular cross-sectional profile with a spherical head, may also have a polygonal profile, in particular a hexagonal or an octagonal profile of the head.

In one embodiment the female locking portion also may have more than two locking hooks, for example, three, four, five or six locking hooks.

In one embodiment the container naturally also may comprise as material stainless steel in place of aluminium.

According to one embodiment, the male press die of the two press dies may have a full-cylindrical protrusion and sharp edges in place of round edges, manufactured, for example, by way of a punching process in order to press the material of the container to be formed outwardly, especially in case of materials of greater thickness, for the further processing steps.

The invention claimed is:

1. A container system comprising a container, at least one (Previously Presented) coupling element, and at least one coupling system for releasably connecting the at least one coupling element to the container, wherein the at least one coupling system includes a male coupling portion formed on the container and a female coupling portion formed on the at least one coupling element, the male and female coupling portions configured to be releasably coupled to and uncoupled from one another, wherein the male coupling portion is integrally formed in a wall of the container and comprises a protruding knob that defines a head and an undercut, and wherein the female coupling portion comprises an expandable spring that defines a recess, wherein the at least one coupling element is couplable to the container by inserting the head into the recess to radially expand the expandable spring and allow the head to pass through the expandable spring, after which the expandable spring retracts into the undercut to engage the head and releasably couple the male coupling portion to the female coupling portion.

2. The container system according to claim 1, wherein the at least one coupling system comprises a push-button system in which the protruding knob protrudes into the recess in a coupled state, the undercut of the protruding knob being encompassed by the female coupling portion in a prestressed manner.

3. The container system according to claim 1, wherein the container is a sterile container and the at least one coupling element is an identification label or an identification bezel or a perforation field cover or a sensor or an identification element or a holding element.

4. The container system according to claim 1, wherein the male coupling portion is formed in one-piece of material in the wall of the container.

5. The container system according to claim 1, wherein the container comprises aluminum or hardened and tempered steel as material.

6. The container system according to claim 1, wherein the protruding knob protrudes from the container perpendicularly relative to a surface of the container and outwards.

7. The container system according to claim 6, wherein the protruding knob has a spherical head with a first diameter and the undercut has a second diameter, the first diameter being greater than the second diameter.

8. The container system according to claim 1, wherein the protruding knob has a flattened head on an upper side of the protruding knob.

9. The container system according to claim 1, wherein the head comprises a bulb section.

10. The container system according to claim 1, wherein the protruding knob is rotationally symmetrical with a circular contour.

11. The container system according to claim 1, wherein the undercut is a circumferential undercut.

12. The container system according to claim 1, wherein the protruding knob comprises an elliptical-shaped cross-section.

13. The container system according to claim 1, wherein the protruding knob comprises a cylindrical section adjacent the undercut, and wherein the undercut separates the cylindrical section from the head.

14. The container system according to claim 1, wherein the expandable spring is an expandable ring.

15. The container system according to claim 14, wherein the expandable ring is a Seeger ring.

16. The container system according to claim 1, wherein the expandable spring comprises a first rounded edge and the undercut comprises a second rounded edge, and wherein the first rounded edge engages the second rounded edge when the male coupling portion is coupled to the female coupling portion.

17. The container system according to claim 1, wherein the wall of the container defines a recess that extends within the protruding knob.

* * * * *